(12) United States Patent
List et al.

(10) Patent No.: US 7,238,192 B2
(45) Date of Patent: Jul. 3, 2007

(54) BLOOD WITHDRAWAL SYSTEM

(75) Inventors: Hans List, Hesseneck-Kailbach (DE); Peter Ruschke, Budenheim (DE); Brian VanHiel, Smyrna, GA (US); Bradley Koeppel, Smyrna, GA (US); Gwenn Kennedy, Ellenwood, GA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 612 days.

(21) Appl. No.: 10/437,717

(22) Filed: May 14, 2003

(65) Prior Publication Data

US 2003/0216767 A1 Nov. 20, 2003

(30) Foreign Application Priority Data

May 16, 2002 (DE) ............... 102 22 235

(51) Int. Cl.
*A61B 17/32* (2006.01)
(52) U.S. Cl. ............. 606/182; 606/167; 606/181
(58) Field of Classification Search ........ 606/181–185, 606/167, 172; 604/136, 137, 22; 600/583
See application file for complete search history.

(56) References Cited

U.S. PATENT DOCUMENTS

| | | | |
|---|---|---|---|
| 3,030,959 A | 4/1962 | Grunert | |
| 3,244,317 A | 4/1966 | Raybin | |
| 3,696,915 A | 10/1972 | Douglas | |
| 3,833,146 A | 9/1974 | Braginetz | |
| 4,416,279 A | 11/1983 | Lindner et al. | |
| 4,442,836 A | 4/1984 | Meinecke et al. | |
| 4,469,110 A | 9/1984 | Slama | |
| 4,535,769 A | 8/1985 | Burns | |
| 4,580,565 A | 4/1986 | Cornell et al. | |
| 4,653,513 A | 3/1987 | Dombrowski | |
| 4,735,203 A | 4/1988 | Ryder et al. | |
| 4,794,926 A | 1/1989 | Munsch et al. | |
| 4,817,603 A | 4/1989 | Turner et al. | |
| 4,821,878 A | 4/1989 | Jones | |
| 4,860,937 A | 8/1989 | Arnold | |
| 4,895,147 A | 1/1990 | Bodicky et al. | |
| 4,998,452 A | 3/1991 | Blum | |
| 5,035,704 A | 7/1991 | Lambert et al. | |
| 5,152,775 A | 10/1992 | Ruppert | |
| 5,269,800 A | 12/1993 | Davis, Jr. | |
| 5,318,584 A | 6/1994 | Lange et al. | |
| 5,464,418 A | 11/1995 | Schraga | |
| 5,478,345 A | 12/1995 | Stone et al. | |
| 5,514,152 A | 5/1996 | Smith | |

(Continued)

FOREIGN PATENT DOCUMENTS

DE 2 803 345 B1 6/1979

(Continued)

*Primary Examiner*—Glenn K. Dawson
*Assistant Examiner*—Kathleen Sonnett
(74) *Attorney, Agent, or Firm*—Bose McKinney & Evans LLP

(57) ABSTRACT

A blood withdrawal system for withdrawing blood for diagnostic purposes including a lancing device having a housing with an opening and a support surface, and a lancet holder movably mounted in the opening including a lancet and a bearing member that rests on the support surface. The device further includes a trigger unit which, when moved linearly, causes a rotational movement to initiate a lancing process.

21 Claims, 4 Drawing Sheets

U.S. PATENT DOCUMENTS

| | | | |
|---|---|---|---|
| 5,527,334 A | 6/1996 | Kanner et al. | |
| 5,531,763 A | 7/1996 | Mastri et al. | |
| 5,554,166 A | 9/1996 | Lange et al. | |
| 5,578,053 A * | 11/1996 | Yoon | 606/185 |
| 5,632,410 A | 5/1997 | Moulton et al. | |
| 5,643,306 A | 7/1997 | Schraga | |
| 5,662,669 A | 9/1997 | Abidin et al. | |
| 5,829,589 A | 11/1998 | Nguyen et al. | |
| 5,908,434 A | 6/1999 | Schraga | |
| 5,951,582 A | 9/1999 | Thorne et al. | |
| 5,984,940 A | 11/1999 | Davis et al. | |
| 6,056,765 A | 5/2000 | Bajaj et al. | |
| 6,156,050 A | 12/2000 | Davis et al. | |
| 6,346,114 B1 * | 2/2002 | Schraga | 606/182 |
| 6,358,265 B1 | 3/2002 | Thorne, Jr. et al. | |
| 6,419,661 B1 * | 7/2002 | Kuhr et al. | 604/207 |
| 6,472,220 B1 | 10/2002 | Simons et al. | |
| 6,514,270 B1 * | 2/2003 | Schraga | 606/182 |
| 6,719,771 B1 | 4/2004 | Crossman | |
| 2002/0169470 A1 | 11/2002 | Kuhr et al. | |
| 2003/0050656 A1 | 3/2003 | Schraga | |
| 2004/0039407 A1 | 2/2004 | Schraga | |

FOREIGN PATENT DOCUMENTS

| | | |
|---|---|---|
| EP | 0 565 970 A1 | 7/1994 |
| EP | 0 582 226 B1 | 10/1997 |
| EP | 1 034 740 A1 | 9/2000 |
| KR | 9605604 Y1 | 7/1996 |
| KR | 9610241 Y1 | 12/1996 |
| KR | 9610335 Y1 | 12/1996 |
| WO | WO 93/09723 | 5/1993 |
| WO | WO 98/14125 | 4/1998 |
| WO | WO 02/30281 | 4/2002 |

* cited by examiner

BLOOD WITHDRAWAL SYSTEM

FIELD OF THE INVENTION

The invention concerns a blood withdrawal system for withdrawing blood for diagnostic purposes.

BACKGROUND OF THE INVENTION

Lancets are used in the sense of the invention as blood withdrawal systems which are used to puncture an appropriate part of the body in order to remove a small amount of blood from a part of the body for analytical or diagnostic purposes. The blood is frequently drawn from a finger or earlobe. In medical practices lancets are used for this which are inserted into an appropriate part of the body by a doctor or laboratory staff either manually or with the aid of a simple apparatus. The lancet must of course be sharp and sterile. Otherwise there are no especially stringent requirements for medical practices since blood is collected from individual patients at large time intervals and the puncture is carried out by specially trained staff. Nevertheless the puncture is frequently associated with considerable pain.

If the blood withdrawal system should be suitable for operation by the patients themselves, this makes much higher demands on the system especially with regard to pain-free and reliable blood withdrawal. The independent use of blood withdrawal systems by patients is carried out especially for so-called home monitoring. In this case the aim is to enable groups of patients that are at special risk to regularly monitor certain analytical values of their blood. This applies among others to diabetics who frequently and regularly check their blood sugar level and adapt it to the requirements by injecting insulin. The insulin requirement depends among other factors on the food intake and physical activity and must be kept as continuously as possible within certain set limits. This is important for the health of the patients and to avoid serious secondary damage such as loss of sight and amputation of parts of the body.

Blood withdrawal systems have been used for a long time which consist of a lancing device and associated lancets that are specially adapted for the respective instrument. A housing of the lancing device contains a lancet drive which mechanically punctures the skin with a lancet. A spring is usually used as a drive element for the lancing movement. In the initial phase of development very simple constructions were commonly used in which the lancet was directly attached to one end of a pressure spring arranged in an elongate housing. Such a blood withdrawal device is disclosed for example in U.S. Pat. No. 4,469,110. However, the use of the described systems show that in particular the requirement for a less painful blood withdrawal cannot be fulfilled.

Recently small, simple-to-operate and relatively low-cost analytical systems have been developed to reduce the pain of puncture which are usually composed of blood test strips and an accompanying evaluation instrument. Such modern blood withdrawal systems are intended to ensure that blood withdrawal is as painless as possible for the patient and is simple to handle. Therefore in the recent prior art numerous different blood withdrawal systems are known which are suitable for generating the incisions required for blood collection in a simple and relatively painless manner.

Such blood withdrawal systems usually comprise a housing with an exit opening for the tip of a lancet and a lancet holder for holding the lancet which can be moved relative to the housing along a predetermined straight puncturing path. The lancet holder is moved during the puncturing and return movement by a lancet drive which has an elastic drive element which is usually a metal spring. In a first position in which the elastic drive element is in a tensioned state, the lancet holder is usually locked by means of a locking device. After such a locking device is released, the elastic drive element relaxes so that the movement of the drive element is converted into a puncturing movement of the lancet drive which moves the lancet held by the lancet holder at high speed along the predetermined lancing path in a puncturing direction until the tip of the lancet emerges from the exit opening of the blood withdrawal system. A wound is generated in a part of the body pressed against the exit opening. Immediately afterwards the lancet is usually retracted by the lancet drive into the housing. The drive units of the modern lancing devices which reduce pain due to a high lancing speed and the retraction of the lancet after the lancing consequently ensure that in the case of the modern lancing devices the blood withdrawal is considerably more pleasant for the patient.

Such blood withdrawal systems of the prior art are described for example in U.S. Pat. Nos. 4,442,836, 4,535,769 and 4,924,897. In the design described in U.S. Pat. No. 4,924,879 a spiral drive spring acts on a wheel whose rotation is converted by means of a lever connected to the wheel into a lancing and retraction movement. It is claimed that the pain is reduced by among others the fact that this movement proceeds very rapidly. However, the construction using precisely manufactured metal parts is complicated and involves many parts. Another disadvantage is that the lancet emerges from the exit opening when the lancet drive is tensioned resulting in a risk of injury for the user.

European Patent No. 0 582 226 describes another lancing device which is suitable for withdrawing blood samples. A piston driven by a spring means is movably mounted within the lancing device. A lancet which emerges through an opening provided in the housing during a lancing process is located at one end of the piston. The outer periphery of the piston has wings of only limited strength which bear against the housing wall of the lancing device. When the lancing process is carried out the piston is moved in the puncturing direction by means of the spring elements thereby destroying the wings of the plunger so that they no longer rest against the housing.

A disadvantage of this prior art device is that the spring elements for driving the piston have to apply sufficient force to first destroy the wings of the piston before the piston can be moved in the lancing direction. Furthermore if the wings are not completely destroyed, this can cause frictional effects when the piston moves within the housing in the lancing direction. Hence the conditions of a lancing process are changed depending on the frictional effects so that undefined force curves act during the lancing process. This influences among others the puncturing speed of the lancet into a part of the skin so that the patient has to expect different levels of pain caused by the puncturing.

In addition the lancet has a sterile protector which has to be removed from the needle tip before use. However, the wings may be damaged as a result of a strong pulling motion and this may accidentally trigger a lancing process. Since the described mechanism is only suitable for disposable lancing devices and it is not possible to retension the lancet due to the destroyed wings on the piston, the unused lancet has to be consequently discarded.

Furthermore U.S. Pat. No. 4,416,279 discloses a blood withdrawal system in which the lancet holder is moved along an inclined ramp located in the housing in an opposite direction to the lancing direction by rotating an external part of the housing. This movement tensions a spring member which serves as the drive element for the lancet holder. The sloping surface protruding into the housing has a plateau on which the lancet holder can be temporarily held after a first rotary movement of the external housing member. In this position the lancet holder is pulled back in the opposite direction to lancing to such an extent that the lancet can be removed from the lancet holder and exchanged. By continuing the rotation the lancet holder is moved further along the sloping surface in the opposite direction to lancing, further tensioning the spring element until the lancet holder is moved beyond the sloping surface and is driven by the force of the spring in the puncturing direction. The lancet tip emerges from the housing.

A disadvantage of the prior art is that the rotational movement of the outer housing member makes it more difficult for the user to handle the blood withdrawal system. In order to tension the blood withdrawal system and simultaneously position the finger pad at the exit opening of the blood withdrawal system, the patient has to position his finger in a holder provided. The holder also serves to fix the position of the blood withdrawal system on the finger tip while the user rotates the outer housing member with the other hand. The said blood withdrawal system proves to be extremely unwieldy and is very difficult to operate particularly by elderly persons.

SUMMARY OF THE INVENTION

In one embodiment, the present invention provides a blood withdrawal system and a method for blood withdrawal in which the described disadvantages of the prior art are avoided. The system and the method are simple. The pain caused by the puncture is reduced by a rapid drive movement of the lancet holder. The construction of the blood withdrawal system is robust and cost-effective.

The invention encompasses a blood withdrawal system having a housing in which an opening is located, and a lancet holder containing a lancet is movably mounted in the housing. The lancet holder has at least one bearing member. A support surface is also located in the housing which is positioned such that the bearing member rests on the support surface in a first position of the lancet holder. The blood withdrawal system also comprises a triggering unit with a release button. The triggering unit converts a linear movement of the release button into a rotation of the bearing member relative to the support surface by which means the lancet holder is transferred into a second position and falls from the support surface. A spring element of the blood withdrawal system is connected to the lancet holder and is transformed by the falling movement of the bearing member from a pretensioned state into an at least partially relaxed state. As a result of the movement of the lancet holder relative to the housing, the tip of the lancet emerges from a bore in a cap connected to an end of the housing so that it can puncture a part of the body that is positioned there.

The blood withdrawal system according to the invention provides a simple robust construction. There are no special requirements with regard to form or material for the bearing member or the support surface. Within the scope of the invention a wide variety of designs are possible which enable the lancet holder to be supported by the support surface. This enables the lancing device to be manufactured with large tolerances without effecting the function of the blood withdrawal device. This simplifies the manufacturing process and hence reduces the production costs for the lancing device. This is a decisive advantage especially for disposable lancing devices that are manufactured in large numbers.

As a result of the described mechanism the puncturing movement of the lancet holder or the lancet is carried out so rapidly that the puncture pain is minimized. As soon as the lancet holder falls from the support surface in the lancing direction, the lancing process is initiated. The potential energy stored in the system is at a maximum. In contrast to the prior art in which the lancing process is for example triggered by breaking off small hooks, the active force of moment of the system is constant in each lancing process since for example additional frictional effects caused by irregular detachment of the small hooks do not occur. This ensures a lancing process under constant, reproducible conditions.

The conversion of a linear movement of the release button into a rotary movement makes the operation of the blood withdrawal system particularly user-friendly since the patient can for example actuate the lancing device by pressing the release button and thus does not have to carry out complicated handling steps.

In principle a wide variety of embodiments of the triggering unit are conceivable for triggering a lancing process which convert a linear movement of the release button into a relative rotation of the bearing member and the support surface. For example a linear movement of the release button can be converted into a rotation of the lancet holder, or embodiments are encompassed in which the support surfaces rotate relative to a part of the housing or relative to the lancet holder. In such a construction actuation of the release button causes a rotary movement of the support surface whereby for example a part of the housing to which the support surface is attached can also be rotated.

In one preferred embodiment the linear movement of the release button occurs perpendicularly to the plane of rotation so that for example the blood withdrawal system is operated by pressing the release button along the puncturing direction.

In one embodiment it has also proven to be expedient for the lancet holder to comprise two bearing members which each rest on a support surface of the housing. This ensures that the lancet holder is supported symmetrically by a simple housing construction. Of course an embodiment is also conceivable which contains more than two bearing members and several support surfaces. In principle the number of bearing members and of the corresponding support surfaces is unlimited so that usually a construction is selected in which the lancet holder is supported optimally and can be manufactured at low costs.

In order to convert the linear movement into a rotary movement of the bearing member and/or the support surface relative to one another, several designs of the triggering unit are also conceivable. In one embodiment of the triggering unit it contains a rotary drive element which is pressed by the linear movement of the release button against the bearing member such that the bearing member falls from the support surface. The rotary drive element for example has an elastic ram and the support surface can contain a depression in which the bearing member of the lancet holder is supported. A linear movement of the release button presses the elastic ram from above against the bearing member of the lancet holder and deforms it in this process. If the bearing member is in a depression of the support surface, the ram can also reach underneath the bearing member due to the deformation or otherwise lever it out of the depression in the support surface. As a result the lancet holder falls from the support surface and a lancing process is triggered. However, a ramp extending into the inside of the housing is also conceivable as a rotary drive element. In this case the ramp is pressed against the bearing member by the linear movement of the release button which pushes it from the support surface and the lancet holder makes a falling movement.

Due to the falling movement of the bearing member and thus of the lancet holder, the spring element is relaxed. In the sense of this invention this is also understood as a process in which the spring element only passes through a relaxed state and is subsequently again converted into a tensioned state.

For example the falling movement of the lancet holder can be stopped by a stop provided for this purpose so that only a defined part of the lancet extends from the housing. The limit stop which consequently determines the puncture depth of the blood withdrawal system can in this connection advantageously be a component of a cap provided for this purpose which is mounted movably on the housing of the system. It is possible for the cap to be attached movably on the housing in or against the lancing direction such that in the case of a limit stop on the housing the distance between the stop and the exit opening of the cap is varied. If the stop is a component of the cap the position of the stop and thus the puncture depth can be changed by moving the cap in the direction of or opposite to the direction of lancing, or it can be changed by a rotation of the cap in which the axial position of the cap remains constant. In such an embodiment the cap contains several stops at different levels which come into use depending on the rotary movement of the cap and which define the puncture depth. Such a system for regulating the puncture depth is described for example in European Patent No. 1 142 534.

After the lancet holder has hit the stop it is usually retracted in the opposite direction as described by means of a return mechanism such that the lancet tip no longer protrudes from the opening of the housing.

In principle the described system is suitable for disposable lancing devices as well as for lancing devices for multiple use. The system is preferably in a tensioned state as soon as the bearing member rests on the support surface. This state has proven to be particularly suitable for disposable lancing devices since a device for tensioning the spring element is often not provided. Disposable lancing devices are then already delivered in a tensioned state to the customer. In this case the customer only has to operate the release button to initiate the lancing process.

In order to avoid contamination the reuse of the disposable lancing device is undesirable and is often actively prevented. This can for example be accomplished by the absence of a tensioning device in the disposable lancing device which simplifies the construction of the lancing device. On the other hand a mechanism is conceivable in which the lancet is actively blocked after use. In this case improper retensioning can be prevented by for example the spring element pressing the bearing member against the support surface from below after the lancing process. Hence this embodiment prevents the bearing member from being positioned on the support surface. In general a wide variety of embodiments are possible that prevent a disposable lancing device from being retensioned.

If the blood withdrawal system is to be suitable for repeated use, the system comprises a device for tensioning the drive element so that the lancing device does not have to be delivered in a tensioned state. In order to avoid unnecessary material stress of the bearing member and the support surface, the drive element in another advantageous embodiment is present in a relaxed or at least partially relaxed state with the bearing member resting on the support surface. Then the drive element is first tensioned in an advantageous manner before or during actuation of the trigger unit before a relative rotation of the lancet holder and the support surface is initiated. Material fatigue of the disposable lancing devices can of course also be avoided by using such a mechanism. However, it may prove to be advantageous to select particularly robust material properties of the bearing members so that the bearing members can withstand the load in a stressed state without difficulty. The tension acting on the bearing members can then be selected such that it does not lead to damage of the bearing members. The puncture speed of the lancing device can be increased according to the tension present in the system to minimize the pain caused by the incision.

Another aspect in constructing a lancing aid is to prevent unintentional triggering of a lancing process particularly when a sterile protector is removed. Various mechanisms are possible for this which ensure the lancet remains in the housing. This protects the user from injury by accidental triggering of the lancing device. Moreover such locking mechanisms ensure the sterility of the lancet before the lancing process. Preferred embodiments of a locking mechanism can comprise locking members as a component of the triggering unit which prevent a rotation of the bearing member and/or the support surface relative to one another as long as the release button is not actuated. Such locking members can, however, also be components of the housing of the lancing device or be located on a detachable sterile protector which is suitable for the sterile storage of the lancet. A combination of the described features is of course also possible such that an interaction of one or more locking members (e.g., on the lancet holder and housing) prevent an accidental triggering of the system. In this connection one of the described embodiments may prove to be advantageous depending on other functions of the lancing device such as a puncture depth adjustment. If the locking mechanism is a component of the sterile protector, a relative rotation of the bearing member and the support surface is prevented as long as the sterile protector has not been detached from the lancet. For example the sterile protector in this case comprises barbs which prevent the lancet holder from moving parallel to the lancing direction. If the support surface advantageously has a depression, this can prevent the bearing members from being lifted out of the depression in the support surface. Such an embodiment proves to be particularly advantageous for example in a puncture depth adjustment in which the axial position of the cap is fixed and cannot be changed.

Another subject matter of the invention is a method for triggering a lancing process with a lancing device. In this case a lancet holder rests on a support surface inside a housing of a lancing device. The operator actuates a trigger unit of the lancing device by means of a linear movement. In this process the linear movement of at least a part of the trigger unit is converted into a rotation of the lancet holder and/or the support surface relative to one another until the lancet holder falls from the support surface and makes a falling movement. As a result of the falling movement a tip of a lancet of the lancet holder emerges through a bore formed in a cap of a housing so that a lancing process can be carried out.

Embodiments of the method are derived as already described.

BRIEF DESCRIPTION OF THE DRAWINGS

The invention is illustrated in the following on the basis of examples in the figures.

DETAILED DESCRIPTION OF EMBODIMENTS OF THE INVENTION

Figure 1:
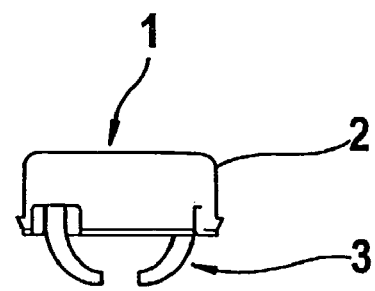
FIG. 1 is an exploded, side view of a blood withdrawal system.

FIG. 1 illustrates the components of a blood withdrawal system before it is assembled. The blood withdrawal system is provided with a housing 9 in which the lancet holder 11 is inserted. The lancet holder 11 is movably mounted in the housing 9 such that it can carry out a lancing process along the puncturing direction. The lancet holder 11 generally includes a body 6, bearing members 5, and a sterile protector 7. For this purpose the system also comprises drive elements which are connected to and act on the lancet holder. In the example shown the drive elements are in each case a spring (4 and 8). In this connection as shown in FIG. 1, the lancet holder 11 can either rest loosely on a spring element or abut a spring element within the scope of the invention without a permanent connection between the spring element and lancet holder 11. In the sense of the invention the connection between the lancet holder 11 and a drive element is characterized in that a force is transferred from the drive element onto the lancet holder 11. However, embodiments are also possible in which the lancet holder 11 is permanently connected to a drive element.

Moreover the lancet holder 11 is positioned in the housing 9 in such a manner that it can rotate about an axis of the lancing direction during the lancing process as illustrated by the following figures. The lancet holder 11 itself has a sterile protector 7 which is placed over a lancet 21 (FIG. 3c) to ensure the sterility of the lancet 21 before use and to prevent accidental injury by the lancet tip.

Figure 5:
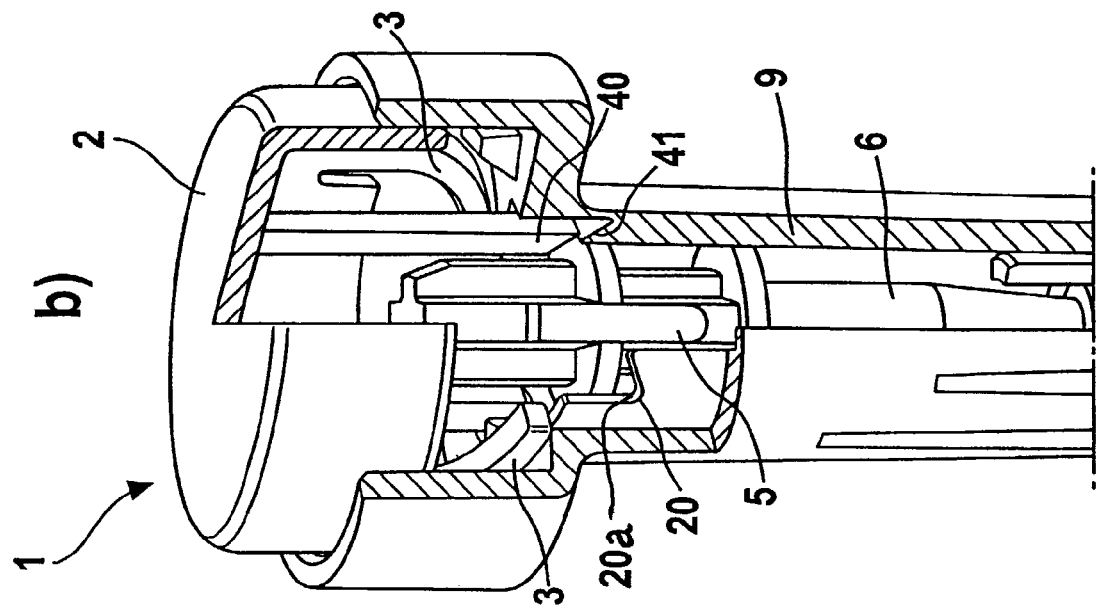
FIGS. 5a and 5b are partially fragmented perspective views of a locking mechanism for preventing an unintentional lancing process.
Figure 5:
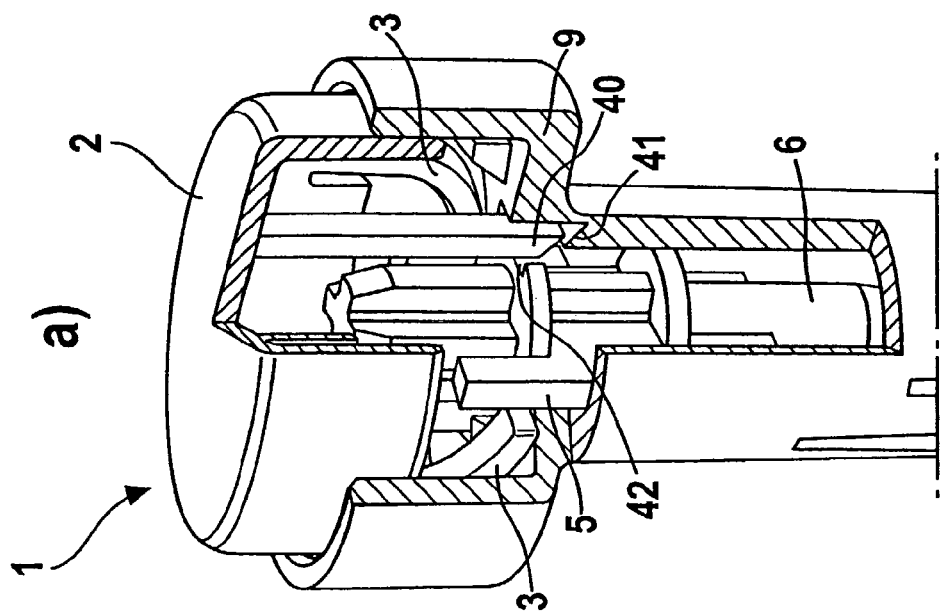

The spring 8 is first inserted into the housing 9. This prevents the lancet 21 from being retracted into the housing 9 after the lancing process when the lancing device is used subsequently. The spring 8 is also referred to as a return spring. The lancet holder 11 is inserted inside the spring 8 and the housing 9. The lancet holder 11 is also provided with bearing members 5 which rest within the housing 9 on support surfaces 20 (FIG. 5) provided for this purpose. The spring 4 as well as the spring 8 interact with the lancet holder 11 in such a manner that when the bearing members 5 rest on the support surfaces 20 within the housing 9, the spring 4 (drive spring) is tensioned whereas the spring 8 (return spring) is relaxed. During the lancing process the drive spring 4 relaxes while accelerating the lancet holder 11. This executes a falling movement and strikes the return spring 8 which is thereby tensioned. The lancet holder 11 falls within the housing 9 down to a stop 30 (FIG. 3c). The lancet holder 11 is pulled back again by the return spring 8 which is then fully tensioned. At this time the drive spring 4 is relaxed.

After the puncture and before the lancing device may be retensioned, both springs (4 and 8) are relaxed and rest against the lancet holder 11.

A cap 10 is movably mounted on the housing 9 at the lower end of the housing 9 such that the extent to which the tip of lancet 21 emerges from the housing 9 can be changed by rotating the cap 10. Different puncture depths can be set for the lancet 21 on the basis of this adjustable distance. The regulation of the puncture depth is also described in the following on the basis of FIG. 4.

At the upper end of the housing 9 the trigger unit 1 closes the upper opening of the housing. In the example shown the trigger unit 1 comprises a release button 2 and two small elastic hooks or arms 3 as rotary drive elements. When the release button 2 is moved along the lancing direction of the lancet 21, the arms 3 cause the lancet holder 11 to rotate.

Figure 2:
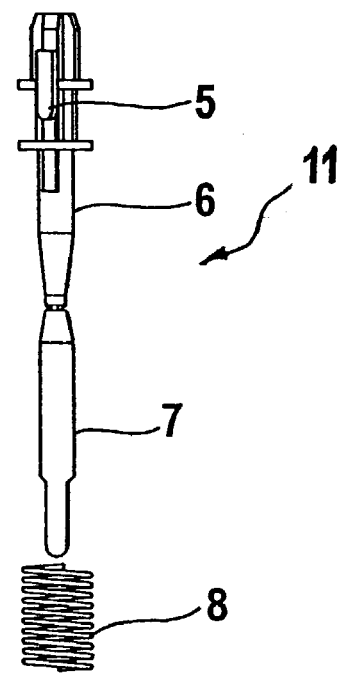
FIG. 2 is a top view of a lancet holder within a housing.
Figure 2:
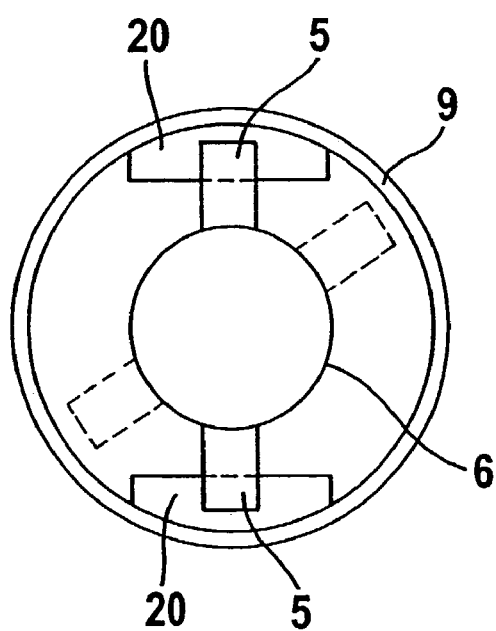

FIG. 2 shows a top-view of a lancing device in which the lancet body 6 is located in a first position (solid lines) in the lancet housing 9. In the example shown the lancet holder body 6 has two bearing members 5 which are in the form of holding arms. In the first position the bearing members 5 rest on the support surfaces 20 of the housing 9. A rotation of the lancet body 6 by pressing button 2 downwardly such that arms 3 engage bearing members 5 and rotate lancet body 6, moves the bearing members 5 into a second position (shown with dashed lines) in which they no longer rest on the support surfaces 20. The lancet holder 11 connected to the bearing members 5 can now move in the lancing direction. A puncture process is carried out by movement of the lancet holder 11 in the lancing direction.

FIGS. 3a through 3c illustrate the triggering of a lancing process based on a lancing device which, as already shown, has a pair of arms 3 as the rotary drive element. FIG. 3a shows the housing 9 of the lancing device in which housing interior can be viewed through a break in the housing wall shown schematically. The housing 9 is closed by a release button 2 and a cap 10. An arm 3 is connected as a rotary drive element to the release button 2. The lancet body 6 which is driven by a spring 4 is located in the interior of the housing 9. The lancet body 6 has a bearing member in the form of a rod by means of which the lancet holder body 6 is mounted on a support surface 20 of the housing 9. The support surface 20 of the housing 9 has a depression 20a which facilitates the positioning of the bearing member 5 on the support surface 20. When the bearing member 5 rests on the support surface 20, the spring 4 is compressed. At this time the arm 3 is positioned next to the bearing member 5.

The lancing process is triggered by pressing the release button 2 along the lancing direction as indicated by the arrow in FIG. 3a. In this process the arm 3 is deformed when the release button 2 is pressed down and engages in the depression 20a of the support surface 20 such that the lancet body 6 rotates and the bearing member 5 falls from the support surface 20 as shown in FIG. 3b. The falling movement causes the lancet body 6 to move in the lancing direction which relaxes the spring 4. The falling movement of the lancet body continues until a stop 30 formed at an end of a slot 22 formed within the housing 9 is reached and struck by the bearing member 5, thereby stopping the falling movement of the lancet body 6. As a result the tip of the lancet 21 emerges from a bore (not shown) formed in the cape 10 attached to the housing 9. The extent by which the lancet tip 21 emerges can be varied by means of the cap 10 which thus enables an adjustment of the puncture depth of the blood withdrawal system as already described. The tip of the lancet 21 is retracted into the housing 9 by means of the return spring 8 so that the lancet does not remain in the body member after perforating a site on the skin. It should be understood that while only one bearing member 5, arm 3, slot 22, and stop 30 is described above, two or more of any or all of these components may be provided consistent with the teachings of the present invention.

Figure 3:
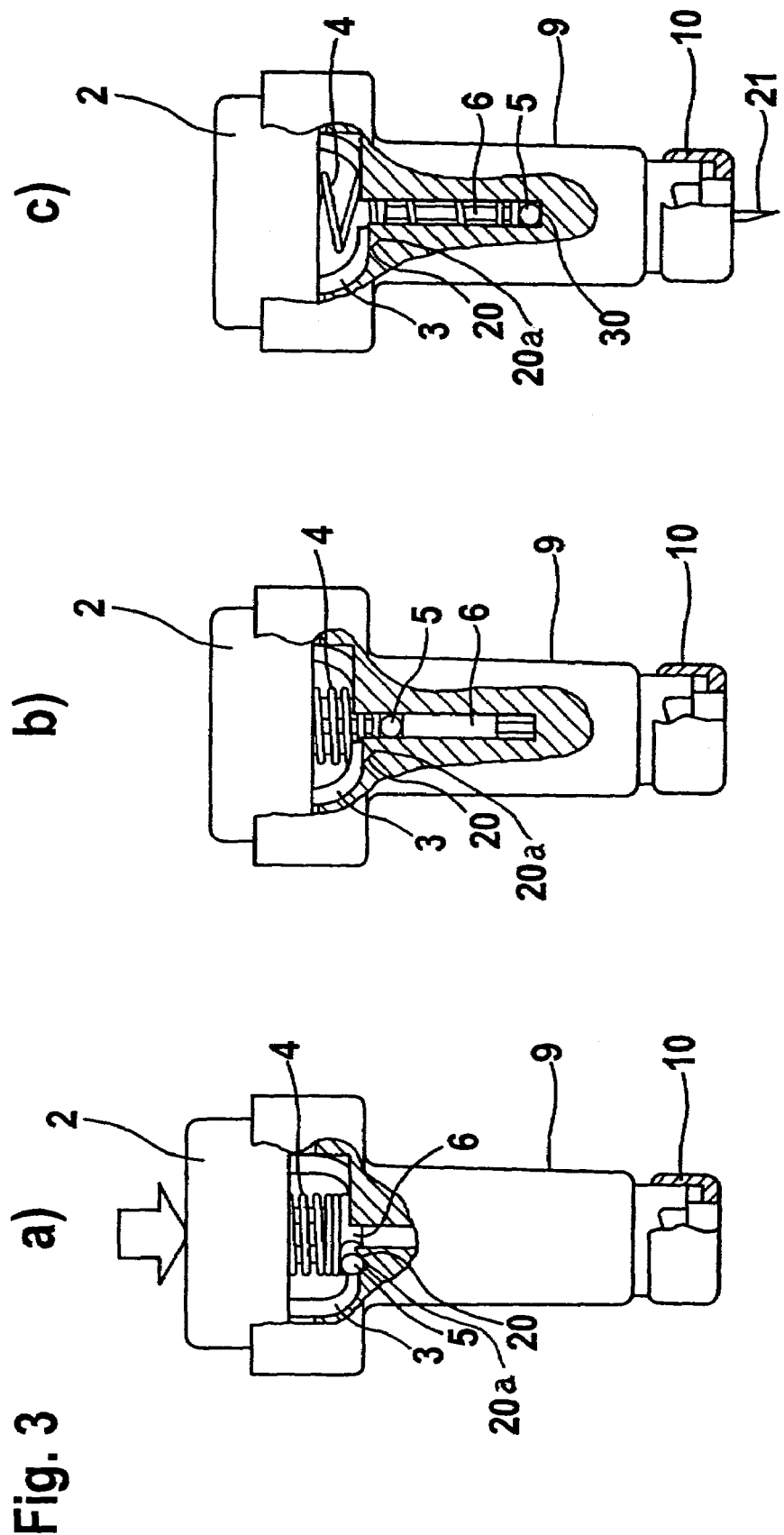
FIGS. 3a-3c are partially fragmented side views of a blood withdrawal system in various positions during a lancing process.
Figure 4:
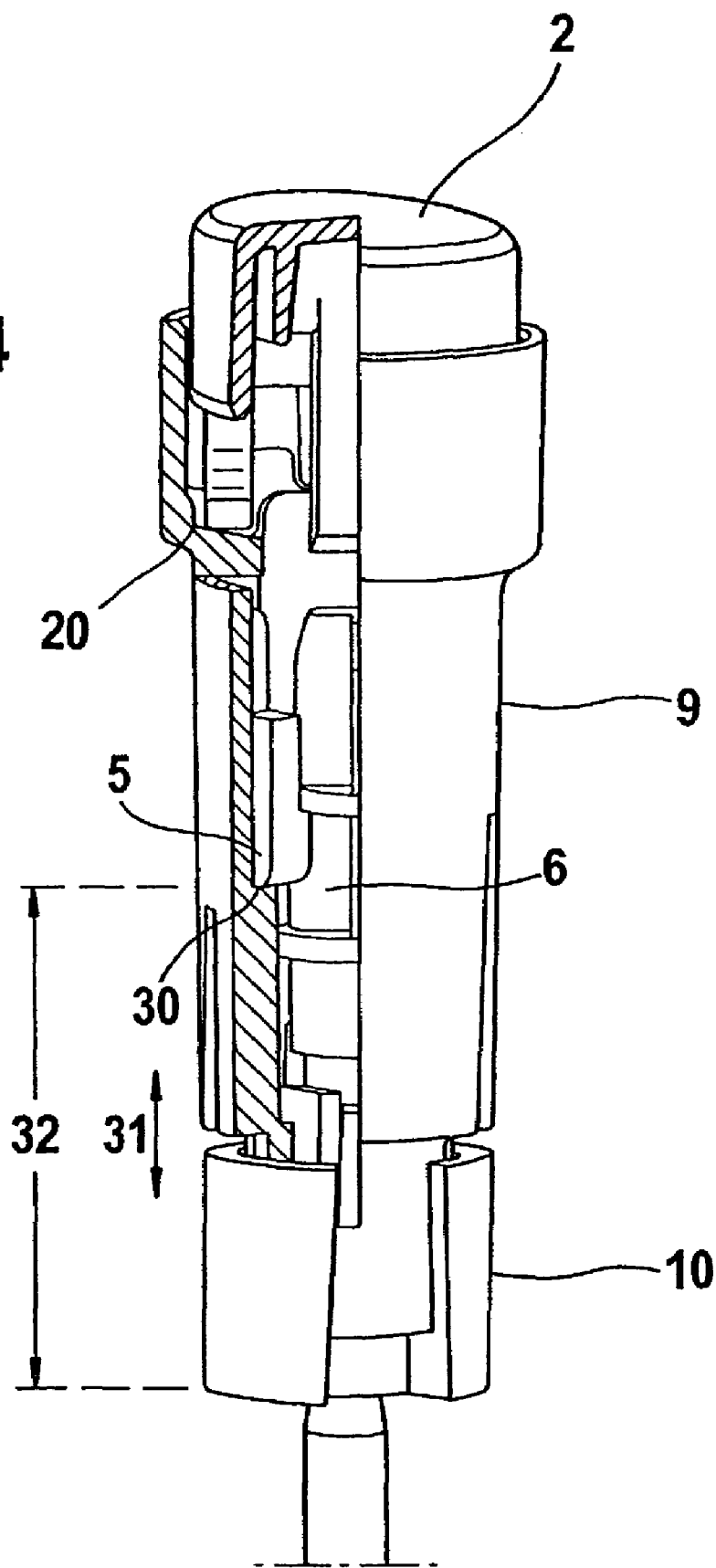
FIG. 4 is a partially fragmented perspective view of a mechanism for adjusting the puncture depth of a system according to the present invention.

FIG. 4 shows a blood withdrawal system having a similar construction as already shown in FIGS. 1 to 3. The system is shown with one side open in order to show an example of a mechanism for regulating the puncture depth. The lancing device shown in FIG. 4 illustrates a state in which the lancet 21 protrudes from the lower end of the housing 9. After the lancing process has been initiated by the release button 2, the lancet body 6 falls along the lancing direction. A falling movement takes place until the lancet body 6 impacts a stop 30 of the housing 9 so that the falling movement is stopped. In the example shown the bearing member 5 which is used to support the lancet holder on the support surfaces 20 is also used as a counter flange with respect to the stop 30. Hence no additional constructional measures are necessary to define the falling movement of the lancet body 6. In the lancing device shown the stop 30 is a component of the housing 9 and cannot be changed. Under these conditions the path along which the lancet body 6 falls is independent of the selected puncture depth. This ensures a constant moment of force in each puncture process. In order to change the puncture depth, the cap 10 which is movably mounted on the housing 9 is rotated, thereby moving the cap 10 along the lancing direction or in the opposite direction as shown by the arrow 31 in FIG. 4. The distance between the stop 30 of the housing 9 and the end of the cap 10 from which the lancet 21 emerges can thus be altered by rotating the cap 10. The distance between the stop 30 and the end of the cap 10 is shown in FIG. 4 by the distance 32. Consequently the extent by which the lancet 21 protrudes from the housing 9 is defined by this distance.

When changing the puncture depth there are several methods that can be used to position the cap 10 along the path 31. For example this can be accomplished by rotating the cap relative to the housing 9. It is, however, also possible for the cap 10 to be moved towards or away from the stop 30 by pulling or pushing in direction 31. In general the cap 10 can be positioned in an infinitely variable manner or in defined steps. Furthermore, the lancing device may also include locking members (not shown) which hold the cap in a predetermined position so that it is not displaced when the cap 10 is placed on a body part. In one embodiment the resulting puncture depth of the lancet is indicated to the user by a scale. A wide variety of mechanisms are in principle possible for adjusting the puncture depth.

For example a mechanism for adjusting the puncture depth is described in the U.S. Pat. No. 4,895,147 which is hereby expressly incorporated herein by reference. In this case the puncture depth of the blood withdrawal system is adjusted by moving a stop of the lancet housing along the lancing direction of the lancing device or in the opposite direction. In this case the lancet body is connected to a control member which falls against the stop when the lancing process is triggered so that the falling movement of the lancet body is stopped. The length of the path along which the lancet body falls is determined in such a mechanism depending on the position of the movable stop. Consequently this results in different moments of acting force depending on the puncture depth.

U.S. Pat. No. 6,056,765, which is hereby expressly incorporated herein by reference, discloses another mechanism for changing the puncture depth of a blood withdrawal system. In this case the lancet is movably mounted in the lancet body. The puncture depth is changed by inserting the needle by different distances into the lancet body whereas the stop for the lancet body is permanently positioned in the housing.

In principle there are a wide variety of methods for adjusting the puncture depth since the blood withdrawal system does not impose any further conditions on the lancing device due to its triggering mechanism that would represent a limitation to such mechanisms.

FIGS. 5*a* and 5*b* illustrate an example of a locking mechanism which prevents unintentional triggering of a lancing process. The figures show the upper region of the housing 9 which effects the triggering of a lancing process. In order to prevent an unintentional triggering, the trigger unit 1 has a locking member 40 in addition to the release button 2 and the rotary drive elements or arms 3. The locking member 40 is in the form of a rod extending into the inside of the housing 9. If the release button 2 is not actuated the locking member 40 is positioned between the housing 9 and the lancet body 6. The lancet body 6 has a notch 42 into which the locking member 40 engages. The described positioning prevents a rotation of the lancet body 6. The locking member 40 is only pressed against a slanted surface 41 of the housing 9 when the release button 2 is pressed in the lancing direction. Further pressure on the release button 2 guides the locking member 40 along the slanted surface 41 and spreads it outwards away from lancet body 6. The lateral stretching of the locking member 40 occurs to such an extent that the locking member 40 no longer engages the notch 42 of the lancet body 6. At the same time the arms 3 are pressed against the bearing members 5 and rotate the lancet body 6 which at this time is no longer blocked by the locking member 40. The rotation occurs until the bearing members fall down from the support surface 20 of the housing 9 and trigger a lancing process. In this case the support surface 20 can, as already shown, have depressions 20*a* in which the bearing members 5 are positioned. However, it is also conceivable that such depressions 20*a* in the support surface are omitted since the locking member 40 ensures a secure mounting of the bearing members 5 on the support surface 20. If such depressions 20*a* in the support surface 20 are omitted, larger tolerances may be allowed in the manufacture of the blood withdrawal system since it is no longer necessary to exactly adapt the lancet body 6 to the housing 9. The manufacturing costs of such a blood withdrawal system may therefore be reduced.

The locking mechanism shown illustrates an alternative embodiment in addition to the locking systems that have already been described. However, in principle any embodiments are conceivable which prevent an unintentional triggering of a lancing process. This is advantageously accomplished in that a rotation of the lancet holder relative to the support surfaces is blocked.

The invention claimed is:
1. A lancing device, including:
   a housing having an opening and a support surface;
   a lancet holder movably mounted in the opening including a lancet and a bearing member configured to rest on the support surface when the lancet holder is in a first position;
   a trigger unit having a release button configured such that when the release button is actuated, linear movement of the release button along a longitudinal axis of the housing is converted into rotational movement of one of the bearing member and the support surface relative to the other of the bearing member and the support surface and causes the lancet holder to move into a second position wherein the bearing member falls from the support surface; and a spring in engagement with the lancet holder such that when the lancet holder is in the first position, the spring is tensioned, and when the lancet holder is moved into the second position, the spring at least partially relaxes thereby moving the lancet holder relative to the housing in a lancing direction such that a tip of the lancet emerges from an end of the housing.

2. The lancing device of claim 1 wherein the spring is connected to the lancet holder.

3. The lancing device of claim 1 wherein the bearing member is urged against an underside of the support surface after the lancet tip emerges from the end of the housing.

4. The lancing device of claim 1 wherein the bearing member undergoes the rotational movement relative to the support surface.

5. The lancing device of claim 1 wherein the lancet holder includes a second bearing member.

6. The lancing device of claim 1 wherein the trigger unit includes a locking member configured to prevent the rotational movement until the trigger unit is actuated.

7. The lancing device of claim 1 wherein the housing includes a locking member configured to prevent unintentional rotation of one of the bearing member and the support surface relative to the other of the bearing member and the support surface.

8. The lancing device of claim 1 further includes a detachable sterile protector for the lancet, the protector including a locking member configured to prevent the rotational movement until the protector is detached.

9. The lancing device of claim 1 wherein the housing includes a stop which stops the movement of the lancet holder in the lancing direction.

10. The lancing device of claim 9 wherein the bearing member engages the stop, thereby stopping the movement of the lancet holder in the lancing direction.

11. A method for triggering a lancing process with a lancing device, including the steps of:
supporting a lancet holder on a support surface in a housing of the lancing device;
actuating a trigger unit of the lancing device such that a release button of the trigger unit carries out a linear movement along a longitudinal axis of the housing;
converting the linear movement of the release button into a rotational movement of one of the lancet holder and the support surface relative to the other of the lancet holder and the support surface, the linear movement causing the lancet holder to move off of the support and carry out a falling movement during which a tip of a lancet of the lancet holder emerges from an end of the housing to carry out a lancing process.

12. The method of claim 11 wherein the linear movement of the release button is substantially perpendicular to a plane of the rotational movement of the lancet holder.

13. A lancing device, including:
a housing having an opening and a support surface;
a lancet holder movably mounted in the opening including a lancet and a bearing member configured to rest on the support surface when the lancet holder is in a first position;
a trigger unit having a release button configured such that when the trigger unit is actuated, linear movement of the trigger unit is converted into rotational movement of one of the bearing member and the support surface relative to the other of the bearing member and the support surface such that the lancet holder moves into a second position wherein the bearing member falls from the support surface, the trigger unit further including a rotary drive element that is moved against the bearing member by the linear movement of the release button, thereby moving the bearing member off of the support surface, the rotary drive element including at least one elastic arm that is deformed by the linear movement of the release button and a slanted ramp that extends into the housing; and a spring in engagement with the lancet holder such that when the lancet holder is in the first position, the spring is tensioned, and when the lancet holder is moved into the second position, the spring at least partially relaxes thereby moving the lancet holder relative to the housing in a lancing direction such that a tip of the lancet emerges from an end of the housing.

14. A lancing device, including:
a housing having an opening and a support surface;
a lancet holder movably mounted in the opening including a lancet and a bearing member configured to rest on the support surface when the lancet holder is in a first position;
a trigger unit having a release button configured such that when the trigger unit is actuated, linear movement of the trigger unit is converted into rotational movement of one of the bearing member and the support surface relative to the other of the bearing member and the support surface such that the lancet holder moves into a second position wherein the bearing member falls from the support surface, the trigger unit further including a locking member configured to engage a recess formed in the lancet holder such that the rotational movement is prevented until the trigger unit is actuated; and a spring in engagement with the lancet holder such that when the lancet holder is in the first position, the spring is tensioned, and when the lancet holder is moved into the second position, the spring at least partially relaxes thereby moving the lancet holder relative to the housing in a lancing direction such that a tip of the lancet emerges from an end of the housing.

15. A lancing device, including:
a housing having an opening and a support surface;
a lancet holder movably mounted in the opening including a lancet and a bearing member configured to rest on the support surface when the lancet holder is in a first position;
a trigger unit having a release button configured such that when the trigger unit is actuated, linear movement of the trigger unit is converted into rotational movement of one of the bearing member and the support surface relative to the other of the bearing member and the support surface such that the lancet holder moves into a second position wherein the bearing member falls from the support surface;
a spring in engagement with the lancet holder such that when the lancet holder is in the first position, the spring is tensioned, and when the lancet holder is moved into the second position, the spring at least partially relaxes thereby moving the lancet holder relative to the housing in a lancing direction such that a tip of the lancet emerges from an end of the housing; and
a detachable sterile protector for the lancet having a locking member configured to prevent the rotational movement until the protector is detached, the protector further including a barb configured to prevent the lancet holder from moving in a direction that is substantially parallel to the lancing direction.

16. A lancing device, including:
a housing having an opening and a support surface;
a lancet holder movably mounted in the opening including a lancet and a bearing member configured to rest on the support surface when the lancet holder is in a first position;
a trigger unit having a release button configured such that when the trigger unit is actuated, linear movement of the trigger unit is converted into rotational movement of one of the bearing member and the support surface relative to the other of the bearing member and the support surface such that the lancet holder moves into a second position wherein the bearing member falls from the support surface, the trigger unit further including a rotary drive element that is moved against the bearing member by the linear movement of the release button, thereby moving the bearing member off of the support surface; and
a spring in engagement with the lancet holder such that when the lancet holder is in the first position, the spring is tensioned, and when the lancet holder is moved into the second position, the spring at least partially relaxes thereby moving the lancet holder relative to the housing in a lancing direction such that a tip of the lancet emerges from an end of the housing.

17. The lancing device of claim 16, wherein the rotary drive element includes at least one elastic arm that is deformed by the linear movement of the release button.

18. A lancing device, including:
a housing having an opening and a support surface;
a lancet holder movably mounted in the opening including a lancet and a bearing member configured to rest on the support surface when the lancet holder is in a first position, the support surface including a depression configured to receive the bearing member when the lancet holder is in the first position;
a trigger unit having a release button configured such that when the trigger unit is actuated, linear movement of the trigger unit is converted into rotational movement of one of the bearing member and the support surface relative to the other of the bearing member and the support surface such that the lancet holder moves into a second position wherein the bearing member falls from the support surface; and
a spring in engagement with the lancet holder such that when the lancet holder is in the first position, the spring is tensioned, and when the lancet holder is moved into the second position, the spring at least partially relaxes thereby moving the lancet holder relative to the housing in a lancing direction such that a tip of the lancet emerges from an end of the housing.

19. A lancing device, including:
a housing having an opening and a support surface;
a lancet holder movably mounted in the opening including a lancet and a bearing member configured to rest on the support surface when the lancet holder is in a first position;
a trigger unit having a release button configured such that when the trigger unit is actuated, linear movement of the trigger unit is converted into rotational movement of one of the bearing member and the support surface relative to the other of the bearing member and the support surface such that the lancet holder moves into a second position wherein the bearing member falls from the support surface;
a spring in engagement with the lancet holder such that when the lancet holder is in the first position, the spring is tensioned, and when the lancet holder is moved into the second position, the spring at least partially relaxes thereby moving the lancet holder relative to the housing in a lancing direction such that a tip of the lancet emerges from an end of the housing; and
a cap movably mounted on the end of the housing, the cap including a bore through which the tip of the lancet emerges when the lancet holder moves in the lancing direction.

20. A method for triggering a lancing process with a lancing device, including the steps of:
supporting a lancet holder on a support surface in a housing of the lancing device;
actuating a trigger unit of the lancing device such that at least a part of the trigger unit carries out a linear movement;
converting the linear movement into a rotational movement of one of the lancet holder and the support surface relative to the other of the lancet holder and the support surface until the lancet holder moves off of the support and carries out a falling movement during which a tip of a lancet of the lancet holder emerges from an end of the housing to carry out a lancing process; and
preventing retensioning of the lancet.

21. A lancing device, including:
a housing having an opening and a support surface;
a lancet holder movably and rotatably mounted in the housing and including a lancet and a bearing member configured to rest on the support surface when the lancet holder is in a first position;
a trigger unit having a release button configured such that when the release button is actuated, linear movement of the release button is converted into rotational movement of one of the bearing member and the support surface relative to the other of the bearing member and the support surface and causes the lancet holder to move into a second position wherein the bearing member falls from the support surface; and
a spring in engagement with the lancet holder such that when the lancet holder is in the first position, the spring is tensioned, and when the lancet holder is moved into the second position, the spring at least partially relaxes thereby moving the lancet holder relative to the housing in a lancing direction such that a tip of the lancet emerges from an end of the housing.

* * * * *